(12) United States Patent
Schweikard

(10) Patent No.: US 7,096,055 B1
(45) Date of Patent: Aug. 22, 2006

(54) METHOD TO CONTROL DELIVERY OF RADIATION THERAPY

(76) Inventor: Achim Schweikard, Vareinastrane 77, D-20357, Hamburg (DE)

( * ) Notice: Subject to any disclaimer, the term of this patent is extended or adjusted under 35 U.S.C. 154(b) by 0 days.

(21) Appl. No.: 09/103,533

(22) Filed: Jun. 24, 1998

(51) Int. Cl.
*A61B 5/05* (2006.01)

(52) U.S. Cl. ............... 600/407; 606/130; 378/65

(58) Field of Classification Search ........... 600/1–8, 600/407–409; 606/130; 128/653.1; 364/413.26, 364/578; 378/65, 152
See application file for complete search history.

(56) References Cited

U.S. PATENT DOCUMENTS 5,458,125 A * 10/1995 Schweikard ............ 128/653.1

* cited by examiner

*Primary Examiner*—John P. Lacyk
(74) *Attorney, Agent, or Firm*—Blank Rome LLP

(57) ABSTRACT

A method is disclosed for controlling the delivery of radiation therapy to a tumor of a patient from one or more beams of ionizing radiation, to conform to a prescribed dosage of radiation for each of predetermined plural respectively shaped portions of the tumor according to the shape and other characteristics of the tumor. A radiation beam is selectively generated from different directions with respect to travel of the beam along a plurality of spatial paths including oscillating and arcuate movements. Parameters of the beam are calculated from conditions of distribution of a target dose, and the cross-section of the beam is adjusted so as to deliver the prescribed dosage of radiation to each of the respectively shaped portions of the tumor on which the beam impinges. The cross-section of the beam is constantly adjusted according to a predetermined area of the tumor which is to receive radiation therapy, and adjusted cross-sections of the beam are moved along selected individual ones of the spatial paths at least one time. Also, movements of the beam along individual spatial paths are split according to the plural portions of the tumor which are to receive different radiation doses. Travel of the beam is controlled along the selected individual paths so as to deliver radiation therapy within the prescribed dosage to each of the plural portions of the tumor in a minimum amount of time. In one embodiment, a micro multi-leaf collimator is placed between the beam and the tumor, and the collimator leaves are adjusted to change the cross-section of the beam impinging on a specified portion of the tumor according to the shape of the specified portion.

17 Claims, 3 Drawing Sheets

METHOD TO CONTROL DELIVERY OF RADIATION THERAPY

BACKGROUND OF THE INVENTION

1. Field of the Invention

The present invention pertains generally to a method for controlling delivery of radiation beams, and, in particular, to a method of controlling delivery of radiation therapy for medical purposes.

2. Description of the Related Art

Radiation therapy is a procedure frequently used in medicine, such as for shrinkage of tumors. Most small tumors are irradiated with high-energy photons. The radiation dose for each tumor and patient must be determined individually. In doing this one must determine from which direction and with which dose weight one is to give radiation treatment, given a known total dose that is to be dispensed.

An especially effective type of radiation therapy is the so-called pendulum irradiation, in which the source of rays traverses along a circular path in a space.

Today, planning the radiation procedure is usually performed manually by the treating physician, who determines both the direction of the single beam and the dose weight. The cross section of the beam used is generally rectangular or circular due to the use of motor-driven leaden jaws or round collimators.

It is, however, necessary to coordinate the shape of the beam with that of the tumor so that, with optimal and exact tumor radiation therapy, the tissue surrounding the tumor and/or the healthy organs are protected against significant exposure to ionizing radiation.

Toward that end, machines have been developed—so-called micro-multileaf collimators (MMLC's)—with which as many different field configurations as desired can be produced. This is accomplished by bringing into the beam path movable, leaf-like lamellae that are independent of each other.

Micro-multileaf collimators are also used with pendulum irradiation. At present it is customary to have up to four circular paths or oscillating motions in the traversed space. Raising the number of circular paths is, however, of crucial significance for increasing the effectiveness of the radiation therapy. Such an increase in the number of circular paths necessitates a considerable increase in the time and complexity of planning the radiation procedure. In part this is because the number of possible path combinations rises exponentially, requiring that the number of possible positions of the lamellae of the MMLC must also be considered. If an MMLC is also used for oscillating motions, the path of each lamella (for example, the number of lamellae may be 52) must also be calculated. It will be apparent, then, that the corresponding planning process is much too involved to rely on manual calculations.

U.S. Pat. No. 5,458,125 of the applicant herein discloses a process for the partial automatic calculation of the direction of the single beam and the weights for static radiation (i.e., no oscillating motion). This planning procedure is only suitable for conical collimators, i.e., for a circular cross section of the beam. The applicant herein has also described a procedure in which only static directions of the single beam are considered, that was published in the conference volume generated by the CAR Conference 97 (held 25–28 Jun. 1997 in Berlin, Germany). Additional prior art will be found in U.S. Pat. Nos. 3,987,281 and 4,868,843.

Planning that takes into consideration dose levels can no longer be carried out manually due to the many possible combinations when using MMLC with pendulum irradiation.

SUMMARY OF THE INVENTION

It is therefore a principal object of the present invention to provide a process that enables a determination of whether the necessary conditions have been fulfilled and to then produce a rapid and accurate calculation of the path for use with MMLC's. Not only circular paths, but also the paths of individual leaves of the MMLC are calculated from the data on the anatomy of the patient.

Moreover, the process according to the invention may take into consideration different dose levels. For example, using this process it is possible to apply radiation therapy accurately to spots to be irradiated when using a very small target dose. This goal is significant in connection with the use of MMLC's, such as to take into consideration in planning the radiation procedure those changes in location of the target (relocatability) attributable to breathing or changes in position of other organs of the patient. The process of the invention may also be used in static situations. Tolerance limits may also be incorporated into the planning mechanism.

According to the invention, a method is provided for controlling an irradiator, in particular, an irradiator utilized for medical purposes such as for cancer therapy, wherein a beam of freely adaptable cross section is produced from different directions, and parameters of the beam are partly or completely automatically calculated from the conditions of a distribution of a target dose.

In a first step of the method of the present invention, tumor boundaries and/or motion tolerances and directions of possible shifting are fed interactively onto a screen by the physician, by previous preparation in which a computer-assisted three-dimensional reconstruction of the tumor region from computerized tomography (CT) and magnetic resonance (MR) data takes place. In the same step the physician can break down the target volume and sub-range steps of different target doses and specify the dose limits.

These specifications are investigated to determine whether they have fulfilled the necessary conditions in accordance with the invention. If the conditions are not fulfilled, the physician is called upon to coordinate the values. Alternatively, these values can be produced partly or completely automatically.

The paths of motion are subdivided into discrete, definite intermediate positions. When using a circular path, the path can be subdivided into 10° steps, with a non-equidistant truncation of the path also being possible.

According to the invention, every discrete direction of a single beam is assigned a variable that describes the dose weight of the direction of the single beam.

The target dose is described by a set of points in space in a target volume and its environment. It can also be described by the specification of the upper/lower limits or by the supplementary conditions of maximizing/minimizing in subregions. Iso-dose regions can also be defined.

If, for example, p is a point in space in a tumor area that is to receive a pre-specified minimum target dose a, then there results a requirement that the dose in p must be larger or equal to a. As a consequence, a series of points according to the invention furnishes a series of equations and inequalities that describe the ordering of the truncated directions of the single beams with the target volume and target dose. When a point p lies in k single beams $s_1, \ldots, s_k$ and the maximum value of the target dose is a, one obtains the following inequality:

$$x_1+x_2+\ldots+x_k \leq a,$$

where $x_1, x_2, \ldots, x_k$ represent the dose weights for each direction of the single beam.

In total, one obtains n equalities and inequalities, in which n is the number of points considered. Whether the system of equations fulfills the necessary conditions is checked by using mathematical methods, in which processes of linear programming as well as genetic algorithms, neuronal networks, or other self-defined processes can be used due to its linearity.

The system can always be solved if a very small set of marginal conditions are required, e.g., if only lower limits for the target dose are defined.

During the process the distribution can be optimized through other marginal conditions.

By solving the system of equations, one obtains dose values for the strength of the dose and the dose weight for each discrete direction of the single beam for each sub-field and each path. The number of the individual doses calculated in this way is equal to the number of the variables, which is, in turn, equal to the product of the number of paths, the number of sub-fields of the target volume, and the number of discrete directions of the single beams.

To reduce the number of variables and be able to carry out the process, all variables according to the invention that correspond to the same path and the same sub-field, but different directions of the single beam, are set equal. As an alternative, the same variable can be used for a path.

In another step variables with a value close to zero are set equal to zero and the distribution is calculated again.

After calculating the distribution of the directions of the single beam and the dose weights, the next step is to calculate the paths of the leaf movements of the MMLC. The supplementary condition for this calculation is time minimization.

Alternatively, before calculating the paths of the leaf movements, the calculated dose distribution can be displayed and modified according to various criteria. Only after confirmation by the user are the paths calculated.

The subdivision of the target volume into areas that are to receive different doses of radiation therapy is important for the paths of the leaf movements. During the first sweep, the field configuration is equal to the configuration of the projection of the tumor, whereby the radiation therapy is the smallest assigned dose. During the subsequent sweeps, the field configuration is matched with different individual iso-dose areas so the smallest possible path sweeps are necessary.

A typical plan with a subdivision of the target region into two subregions consists of four paths in space. This situation corresponds to eight variables, whereby each path is used twice with a different position of the collimator and consequently a different field configuration.

BRIEF DESCRIPTION OF THE DRAWINGS

The invention is illustrated in greater detail in the text below, in conjunction with the drawings, in which.

DETAILED DESCRIPTION OF THE PRESENTLY PREFERRED EMBODIMENT AND METHOD OF THE INVENTION

Figure 1:
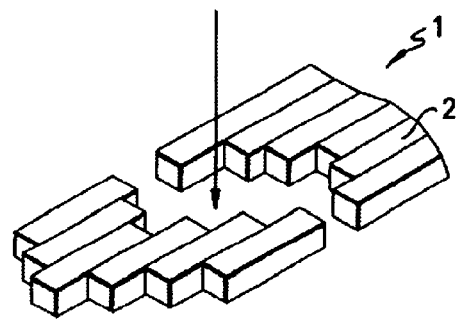
FIG. 1 is a diagrammatic perspective top view of a micro-multileaf collimator (MMLC)

As is shown in FIG. 1, a micro-multileaf collimator MMLC 1 consists of several individual leaves or lamellae 2, which can be brought into the beam path independent of each other through conventional motor-driven means (not shown). In this way, as many field configurations as desired can be produced and, in particular, the field configuration can be matched to the projection of the tumor shape and the tumor area which is to receive the radiation therapy.

Figure 2:
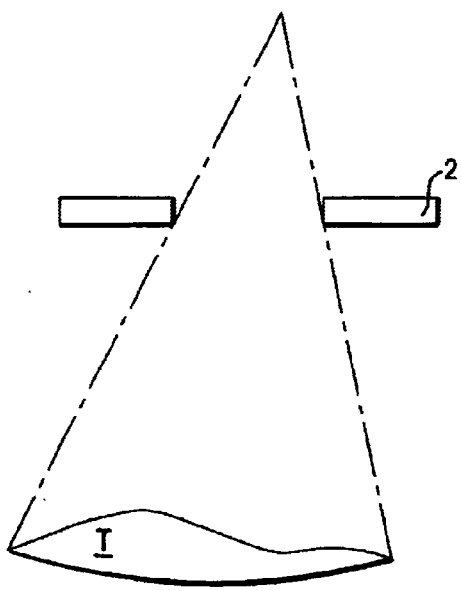
FIG. 2 is a diagrammatic representation of the way a micro-leaf collimator functions.

The way in which MMLC 1 functions will be better understood by reference to FIG. 2. The leaves 2 are moved in such a way that the cross section of the beam matches the shape of the tumor T.

Figure 3:
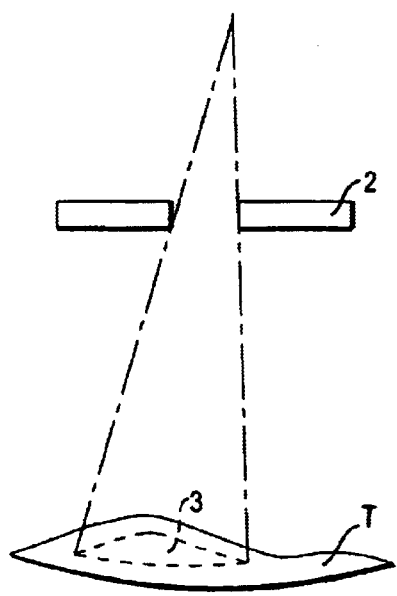
FIG. 3 is a diagrammatic representation of the way a micro-leaf collimator assigned with different doses functions.

If, for example, an inner area of the tumor T is to receive a different, higher dose by using MMLC 1, as is shown in FIG. 3, the inner area 3 is first given a radiation dose that corresponds to the difference between the dose assigned to the inner area and the dose assigned to the outer area. Finally, by matching the cross section of the beam to the entire tumor area T again, the entire tumor receives the remaining dose of radiation therapy—the dose corresponding to that assigned to the outer area.

Figure 4A:
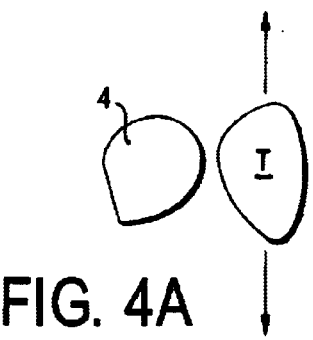
FIGS. 4a and 4b are diagrammatic views illustrating the movement tolerance of a tumor.
Figure 4B:
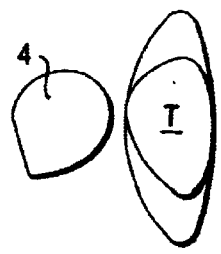

According to the process of the invention, as a first step tumor boundaries and/or movement tolerances and the directions of a possible shifting are introduced interactively onto a computer screen by the physician after obtaining a computer-assisted three-dimensional reconstruction of the tumor region from CT and MR data. FIG. 4a shows a tumor T and its possible direction of real-time movement in or on the patient's body—e.g., as a result of breathing by the patient. In FIG. 4b, a tolerance range is introduced that is plotted such a way that a movement of the tumor is taken into consideration without including a neighboring organ 4 that must not be irradiated during radiation therapy.

Figure 5:
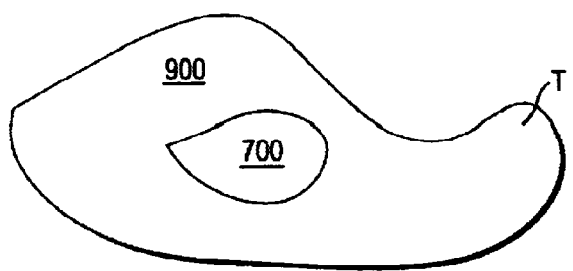
FIG. 5 is a perspective view of a tumor in which the central area is to receive a lower dose than the outer area.
Figure 6:
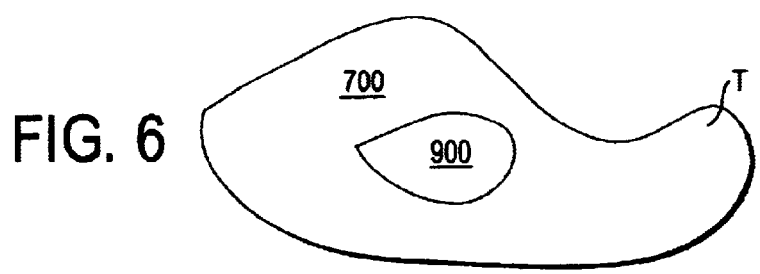
FIG. 6 is a perspective view of a tumor in which the central area is to receive a higher dose than the outer area.

Further according to the process of the invention, the target volume of the tumor T is subdivided into subareas of different target doses, and the dose limits are specified, by the physician. This is represented diagrammatically in FIGS. 5 and 6. In FIG. 5, the inner area is to receive a smaller dose of radiation than the outer area. In contrast, FIG. 6 depicts a situation a larger dose of radiation therapy is to be delivered to the inner area than to the outer area. The number of areas of different target doses is unlimited. In this connection, a grid-like subdivision of the tumor is possible.

According to another aspect of the invention, this information can be examined to determine whether it fulfills the necessary conditions. If the conditions are not fulfilled, the doctor is called upon to adjust the respective values so they match. Alternatively, these values can be produced partly or wholly automatically.

Figure 7:
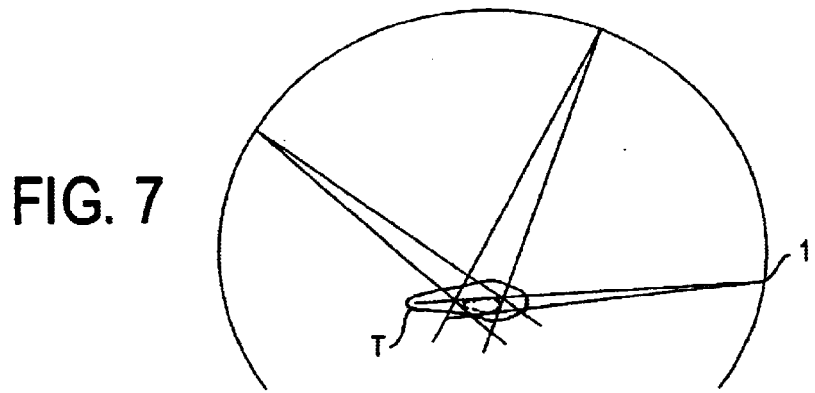
FIG. 7 is a diagrammatic view of a circular path with discrete intermediate positions of a tumor subdivided into two areas receiving different doses.

Referring to FIG. 7, the movement paths are subdivided into discrete, definite intermediate positions. In the case of a circular path, for instance, the path can be subdivided into 10° steps, whereby a non-equidistant truncation of the path is also possible.

A further aspect of the invention calls for each discrete direction of the single beam to be assigned a variable value that describes the dose weight of that direction of the single beam. Finally, within the framework of the process according to the invention the variables are assigned values that satisfy the conditions of the target dose distribution. Weights and directions of the single beam are calculated first, and after they are determined, the optimal movements of the lamellae are calculated.

The target dose is described by a set of points in space in the target volume and its environment. It can also be described by specifying the upper/lower limits or the supplementary conditions—i.e., maximization/minimization in subregions.

When a point p of the tumor area lies in k single beams $s_1, \ldots S_k$, and the target dose has a maximum value of a, one obtains the following inequality:

$$x_1 + x_2 + \ldots + x_k \leq a,$$

where $x_1, x_2, \ldots, x_k$ represents the dose weight for each direction of the single beam.

In total, n equations or inequalities are obtained, where n is the number of the points under consideration. If the system of equations is determined by mathematical methods to be sufficient to fulfill the necessary conditions, the equations are then solved to obtain dose values for the dose strength and dose weight for each discrete direction of each sub-field and each path. The number of single doses calculated in this way is equal to the number of variables, which is, in turn, equal to the product of the number of paths, the number of sub-fields on the target volume, and the number of the discrete directions of the single beam.

After calculation of the distribution of the directions of the single beam and the dose weight, the paths of the leaf movements of the MMLC are calculated. A supplementary condition for this calculation is time minimization of the radiation therapy procedure.

Different ways of subdividing the target volume and different dose weight subdivisions lead to different total radiation therapy times. An important part of the process according to the invention is the partial or completely automatic calculation of a suitable subdivision and/or suitable movements of the lamellae, which lead to a global minimization of the total radiation therapy time.

Figure 8:
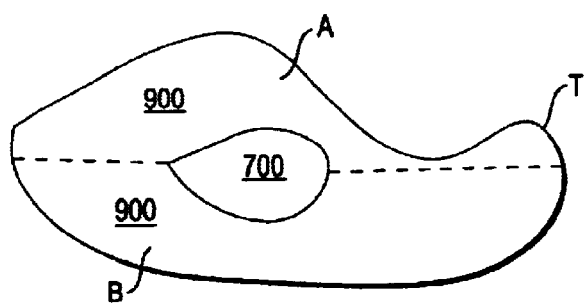
FIG. 8 is a perspective view of the tumor of FIG. 5 with a subdivision suitable for irradiation.

For this purpose, one must take into consideration that the length of time of the radiation therapy to dispense dose a in a point p is directly proportional to a, but the radiation time does not depend on the size of the field at all or is only negligibly dependent on it. FIG. 8 shows a tumor in which a central area receives a smaller dose than the boundary area. In this case a dose of 700 units (e.g., CGY's) is to be attained in the center and a dose of 900 units in the boundary areas.

One possibility for administering radiation therapy is to divide it up so the upper subregion A receives a radiation treatment of 900 units, the inner subregion 700 units, and the lower region B 900 units. Due to the proportionability, the total time is 900+700+900 units. For this first example, then, the total time amounts to 2,500 units of time.

If, however, another plan is used, a shorter total time results. If one first applies radiation therapy to the entire area—i.e., 700 units to the inner, upper, and lower region— and then 200 to the upper area and finally 200 to the lower region, a total time of 700+200+200=1,100 units of time is yielded. The sequence of the three steps does not play any role.

According to the invention the process for calculating the lamellae positions consists in the following steps.

All positions of the collimator in which each series of lamellae approximates a field boundary are calculated. This leads to a finite number of collimator positions. A variable is used for each such position pattern. This variable designates the length of time that each position pattern receives radiation therapy. If the required target dose in a point p equals a, a supplementary condition results, requiring that the total sum of the dose contributions from all position patterns in which p lies in the beam must equal a. The sum of all the variables is then minimized. Because all equations or inequalities are linear, linear programming methods or other suitable processes can be used. The result is the ability to calculate planes that are minimized with respect to time on a global basis, because, for example, linear programming processes yield a global minimum. For this reason very complex movement patterns of the collimator lamellae, in which the target region is made of many subregions of different doses, can also be determined.

Figure 9:
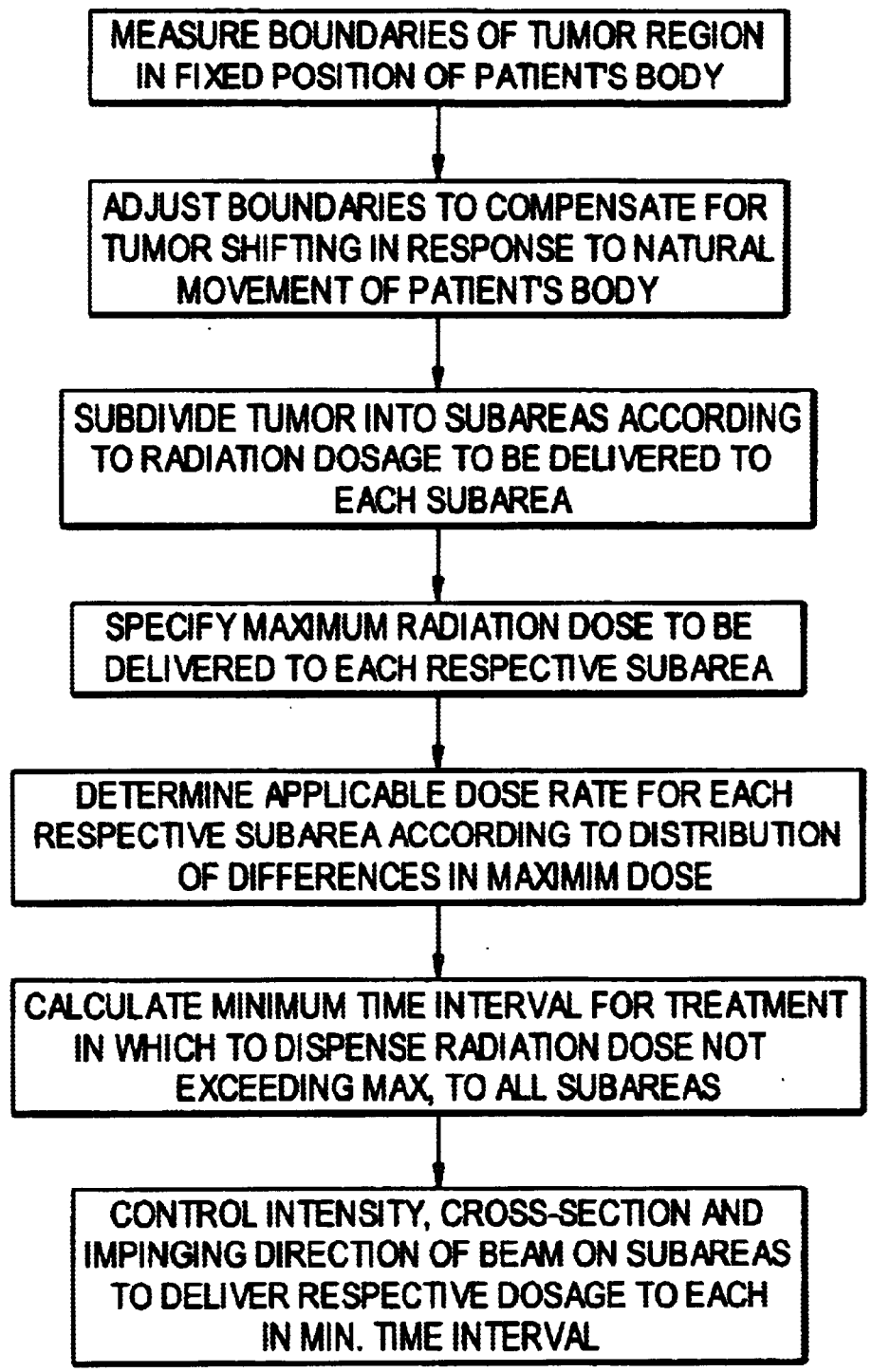
FIG. 9 is a is a flow chart illustrating an exemplary radiation therapy process for controlling the delivery of a beam of radiation of adaptable cross-section from any of a plurality of different directions to impinge on a preselected tumor region in a patient's body in a treatment session.

FIG. 9 is a flow chart derived from the foregoing description, illustrating an exemplary radiation therapy process for controlling the delivery of a beam of radiation of adaptable cross-section from any of a plurality of different directions to impinge on a tumor in a patient's body in a treatment session.

In the process, the boundaries of the tumor are measured based on a selected fixed position of the patient's body; and thereafter adjusted to compensate for shifting of the tumor in response to natural movement such as patient breathing. The area occupied by the tumor is subdividied into subareas based on differences in radiation dosage to be delivered to them from the beam, and a maximum radiation dose is specified for delivery to each subarea in the treatment session.

The dose rate applicable for each subarea for a plurality of discrete directions of beam impingement along a selected travel path in a predetermined volume of space including the tumor is determined according to the distribution of the differences in radiation dosage for the respective maximum dose to be delivered to each subarea. A minimum time interval for the treatment session is calculated for dispensing a radiation dosage not more than the maximum dose to be delivered to all subareas of the tumor. And the intensity, cross-section and direction of impingement of the radiation beam on the subareas are controlled to deliver the respective radiation dosages throughout the tumor in substantially that minimum time interval.

What is claimed is:

1. A radiation therapy process for controlling the delivery of a beam of radiation of adaptable cross-section from any of a plurality of different directions to impinge on a preselected tumor region in a patient's body in a treatment session, said process comprising measuring the boundaries of said tumor region based on a selected fixed position of the patient's body; adjusting said boundaries to compensate for shifting of said tumor region from movement during patient breathing and other natural movements; subdividing the area occupied by said tumor region into subareas based upon differences in radiation dosage to be delivered thereto from said beam; specifying a maximum radiation dose to be delivered to each respective subarea in the treatment session; determining the dose rate applicable for each of said subareas for a plurality of discrete directions of impingement of said beam along a selected travel path thereof in a predetermined volume of space onto the respective subareas of said tumor region according to the distribution of said differences in radiation dosage for the respective maximum dose to be delivered thereto; calculating a minimum interval of time for said treatment session in which to dispense a radiation dosage not more than said maximum dose for all said subareas of said tumor region; and controlling the intensity, cross-section and direction of impingement of said radiation beam on said subareas, to deliver the respective radiation dosages throughout said tumor region in substantially said minimum interval of time.

2. The radiation therapy process of claim 1, wherein the step of controlling said cross-section of said radiation beam includes adjusting the positions of leaves of a micro-multileaf collimator on which said beam impinges before impinging on said tumor region.

3. A method for controlling the delivery of radiation therapy to a tumor of a patient from one or more beams of ionizing radiation, to conform to a prescribed dosage of radiation for each of predetermined plural respectively shaped portions of the tumor according to the shape and other characteristics of the tumor, said method comprising the steps of:

generating a radiation beam selectively from different directions with respect to travel of the beam along a plurality of spatial paths including oscillating and arcuate movements, to impinge on said plural portions of said tumor, calculating parameters of said beam from conditions of distribution of a target dose, and adjusting the cross-section of said beam so as to deliver said prescribed dosage of radiation to each of said predetermined plural respectively shaped portions of the tumor.

4. The method of claim 3, including the step of constantly adjusting said cross-section of said beam according to a predetermined area of aid tumor which is to receive said radiation therapy.

5. The method of claim 4, including the step of moving adjusted cross-sections of said beam along selected individual ones of said spatial paths at least one time.

6. The method of claim 5, including the step of splitting movements of said beam along individual ones of said spatial paths according to said predetermined plural respectively shaped portions of said tumor which are to receive different radiation doses from said beam.

7. The method of claim 3, including the step of controlling travel of said beam along said selected ones of said individual paths so as to deliver said radiation therapy within said prescribed dosage to each of said predetermined plural respectively shaped portions of the tumor in substantially a minimum amount of time.

8. The method of claim 4, including the step of placing a micro-multileaf collimator between said beam and said tumor, and adjusting leaves of said micro-multileaf collimator to change the cross-section of said beam impinging on a specified portion of said tumor according to the shape of said specified portion.

9. A process for treating malignant tumors with a beam of ionizing radiation, comprising the steps of:

controlling said radiation beam to render it of freely adaptable cross section according to predetermined conditions of distribution of a target dose to be delivered to a tumor, so as to control the prescribed dose and distribution of radiation delivered from said beam based on shape and differing needs of treatment of various portions of said tumor, including interposing a radiation-opaque device of adjustable shape in the path of said beam, and automatically adjusting said shape of the interposed device to enable delivery of radiation distributed in increments from a predetermined maximum dosage to a predetermined minimum dosage according to a prescribed pattern for said differing needs of treatment of said various portions of the tumor.

10. The process of claim 9, including adapting said beam for travel along different spatial paths according to said conditions of distribution.

11. The process of claim 9, including adapting said beam for travel in oscillating and arc-like movements according to said conditions of distribution.

12. The process of claim 9, including continuously adjusting said cross-section of the beam for projection on various portions of the tumor according to their respective differing needs of treatment.

13. The process of claim 12, including moving said adjusted cross sections of the beam a predetermined number of times along individual ones of plural paths.

14. The process of claim 13, including splitting individual path movements are into several parts for delivering predetermined different radiation doses to said various portions of the tumor.

15. The process of claim 9, including performing said step of controlling said radiation beam to continuously adjust its cross-section in a manner to optimize the time interval of treatment of the tumor.

16. The process of claim 9, including interactively displaying boundaries of the tumor on a computer monitor screen.

17. The process of claim 9, including using a micro-multileaf collimator as said device.

* * * * *